United States Patent
McCusker et al.

(10) Patent No.: US 7,390,310 B2
(45) Date of Patent: Jun. 24, 2008

(54) SHUNT VALVE LOCKING MECHANISM

(75) Inventors: Daniel McCusker, Bridgewater, MA (US); Alan J. Dextradeur, Franklin, MA (US); Rainuka Gupta, Cambridge, MA (US); Carleton Bryan Southworth, Warsaw, IN (US)

(73) Assignee: Codman & Shurtleff, Inc., Raynham, MA (US)

( * ) Notice: Subject to any disclaimer, the term of this patent is extended or adjusted under 35 U.S.C. 154(b) by 882 days.

(21) Appl. No.: 10/192,394

(22) Filed: Jul. 10, 2002

(65) Prior Publication Data
US 2004/0010219 A1    Jan. 15, 2004

(51) Int. Cl.
*A61M 5/00* (2006.01)
*F16K 31/12* (2006.01)
*F16F 35/00* (2006.01)

(52) U.S. Cl. .............................. 604/9; 604/8; 604/247; 251/12; 251/58; 251/59; 251/213; 137/383; 137/384.8; 137/385

(58) Field of Classification Search ............... 604/8–10, 604/19, 27, 28, 30–34, 48, 93.01, 183, 186, 604/207, 256, 211–212, 167.01, 167.02, 604/167.03, 167.05, 246–250, 264, 523, 604/537; 251/4, 12, 59, 58, 56
See application file for complete search history.

(56) References Cited

U.S. PATENT DOCUMENTS

| 4,615,691 | A  |   | 10/1986 | Hakim et al. |     |
|-----------|----|---|---------|--------------|-----|
| 5,637,083 | A  | * | 6/1997  | Bertrand et al. | 604/9 |
| 5,643,194 | A  | * | 7/1997  | Negre         | 604/8 |
| 6,840,917 | B2 | * | 1/2005  | Marion        | 604/9 |
| 2002/0026139 | A1 | * | 2/2002 | Bertrand et al. | 604/9 |

* cited by examiner

*Primary Examiner*—Tatyana Zalukaeva
*Assistant Examiner*—Phil Wiest
(74) *Attorney, Agent, or Firm*—Nutter McClennen & Fish LLP

(57) ABSTRACT

A locking assembly is provided to simply and effectively prevent any unintentional adjustment of the adjustable valve mechanism in a fluid flow control device, without compromising the function of the device. The locking assembly generally includes at least one gripping arm for frictionally engaging at least a portion of the adjustable valve mechanism, and an actuating mechanism for controlling the deployment and release of the gripping arm. The locking assembly prevents unintentional adjustments that can adversely affect the pressure settings of the fluid flow control device. In particular, the locking assembly prevents unintentional adjustment, such as may be caused by the presence of a strong external magnetic field. The locking assembly can be easily disengaged, such as through the application or removal of an external mechanical force, to allow a clinician to adjust the pressure settings of the fluid flow control device as necessary.

13 Claims, 7 Drawing Sheets

SHUNT VALVE LOCKING MECHANISM

CROSS-REFERENCE TO RELATED APPLICATIONS

Not applicable

STATEMENT REGARDING FEDERALLY SPONSORED RESEARCH

Not applicable

FIELD OF THE INVENTION

The present invention relates generally to medical devices for directing bodily fluids from one region of a patient to another region. More specifically, this invention relates to shunt systems having an adjustable shunt valve to control the flow of fluid through the system and, even more specifically, a locking mechanism to control the adjustment of the shunt valve.

BACKGROUND OF THE INVENTION

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain is blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the bloodstream.

Generally, the shunt valve, which can have a variety of configurations, is effective to regulate the flow rate of fluid through the shunt system. In some shunt valve mechanisms, the fluid flow rate can be proportional to the pressure difference at the valve mechanism. These shunt valve mechanisms permit fluid flow only after the fluid pressure has reached a certain threshold level. Thus, when the fluid pressure is slightly greater than the threshold pressure level, the fluid flow rate is relatively low, but as the pressure increases, the fluid flow rate simultaneously increases. Typically, the shunt valve will allow fluid to flow normally until the intracranial pressure has been reduced to a level that is less than the threshold pressure of the shunt valve, subject to any hysteresis of the device.

Shunt valves can be designed to allow adjustment of the threshold pressure level at which fluid flow will commence. It is generally preferred to allow external adjustment of the pressure threshold to avoid invasive surgical procedures. In some shunt systems, the shunt valve contains a magnetized rotor to control the pressure threshold of the valve. Physicians can then use an external adjustment mechanism, such as a magnetic programmer, to adjust the pressure threshold of the shunt valve. However, these magnetized rotors can be unintentionally adjusted in the presence of a strong external magnetic field, such as during an MRI procedure. Unintentional adjustment of the pressure threshold could lead to either the overdrainage or underdrainage of CSF, which can result in dangerous conditions, such as subdural hematoma.

Attempts have been made to provide a locking mechanism that prevents unintentional valve adjustment, even in the presence of a strong external magnetic field, while simultaneously allowing intentional adjustment of the pressure threshold. One such approach has been detailed in U.S. Pat. No. 5,643,194, in which Negre discloses a locking means having two opposed micro-magnets mounted on the rotor. In the presence of a bi-directional magnetic field, these micro-magnets move linearly in the rotor, in a substantially radial direction, to activate the locking means. However, the Negre locking means does not eliminate the risk of inadvertent valve adjustment in the presence of a strong external magnetic field.

Another approach has been described in U.S. Pat. No. 5,637,083, in which Bertrand et al. disclose a valve that includes means for locking the rotor assembly in a desired position. This locking means uses a pin having a first end adapted to engage a series of detents in an outer peripheral surface of the rotor assembly, thereby preventing the rotor assembly from rotating. The locking means is disengaged by a pin-actuating means having two levers that move the pin from a first, extended position, i.e., within the detent(s) in the outer peripheral surface, to a second, retracted position. The first lever is a pivotable lever having a shaft adapted to engage a second end of the pin, while the second lever is a manually actuated lever that is biased to urge the pin into the first, extended position. This manually actuated lever, however, is located within the valve chamber that is used to pump, or flush, fluid from the shunt valve. Thus, by virtue of its location within the pumping chamber, the manually actuated lever, and consequently the pin-actuating means, can impair or inhibit the function of the pumping chamber.

Accordingly, there exists a need for a shunt valve having an improved locking mechanism that simply and effectively prevents unintentional adjustment of the valve pressure threshold, yet still allows simple, non-invasive adjustment of the pressure threshold of the valve. There is also a need for a locking mechanism that does not compromise or inhibit normal operation of the shunt valve. Furthermore, there exists a need for a locking mechanism that has been designed to allow a physician to easily determine the location of the locking mechanism. Finally, there exists a need for a locking mechanism that has little or no artifact, or extraneous signal, during various radiological imaging techniques, including X-Ray or MRI, and therefore, will not interfere with, or compromise necessary medical procedures.

SUMMARY OF THE INVENTION

The present invention overcomes the disadvantages that are inherent in prior art fluid management systems by providing a locking assembly that simply and effectively prevents any unintentional adjustment of an adjustable valve mechanism in a fluid flow control device, without compromising the function of the fluid flow control device. The locking assembly of the present invention generally includes at least one gripping arm for frictionally engaging at least a portion of the adjustable valve mechanism, and an actuating mechanism for controlling the deployment and release of the at least one gripping arm. The locking assembly prevents unintentional adjustments that can adversely affect the pressure settings of the fluid flow controlling medical device. In particular, the locking assembly prevents unintentional adjustment in the presence of a strong external magnetic field, such as for example, the strong unidirectional magnetic field in an MRI procedure. The provided locking assembly allows a clinician to easily disengage the locking assembly, such as through the application or removal of an external mechanical force, thereby allowing the clinician to adjust the pressure settings of the fluid flow control device as necessary.

Further features of the invention, its nature and various advantages will be more apparent from the accompanying drawings and the following detailed description of the drawings and the preferred embodiments.

DETAILED DESCRIPTION OF THE INVENTION

The locking assembly of the present invention stably maintains an adjustable valve mechanism of an adjustable fluid flow control device in a desired position, thereby preventing any unintentional adjustments of the fluid flow control device. Generally, the locking assembly of the present invention includes at least one gripping arm that is operatively joined to an actuating mechanism and can control the deployment and release of the at least one gripping arm. The locking assembly prevents unintentional adjustments that can adversely affect the pressure settings of the fluid flow controlling medical device. In particular, the locking assembly prevents unintentional adjustment in the presence of a strong external magnetic field, such as for example, the strong unidirectional magnetic field encountered in an MRI procedure. The locking assembly can be easily disengaged, through the application or removal of an external mechanical force, thereby allowing a clinician to adjust the pressure settings of the fluid flow control device.

Figure 1A:
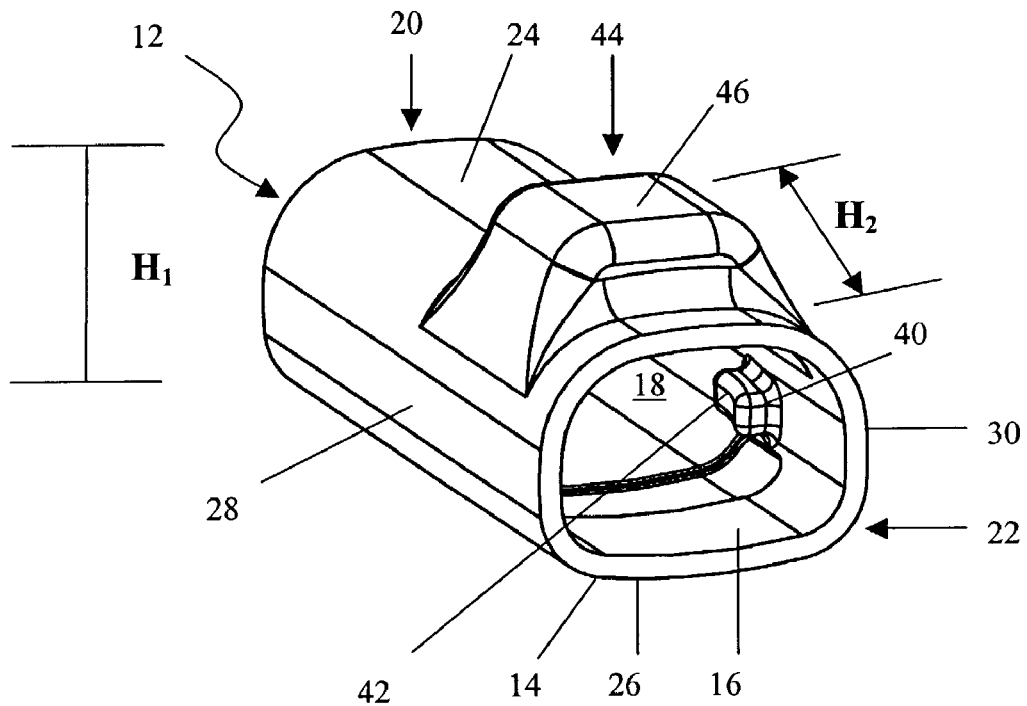
FIG. 1A is a perspective view illustrating the housing with the locking assembly according to one embodiment of the present invention.
Figure 1B:
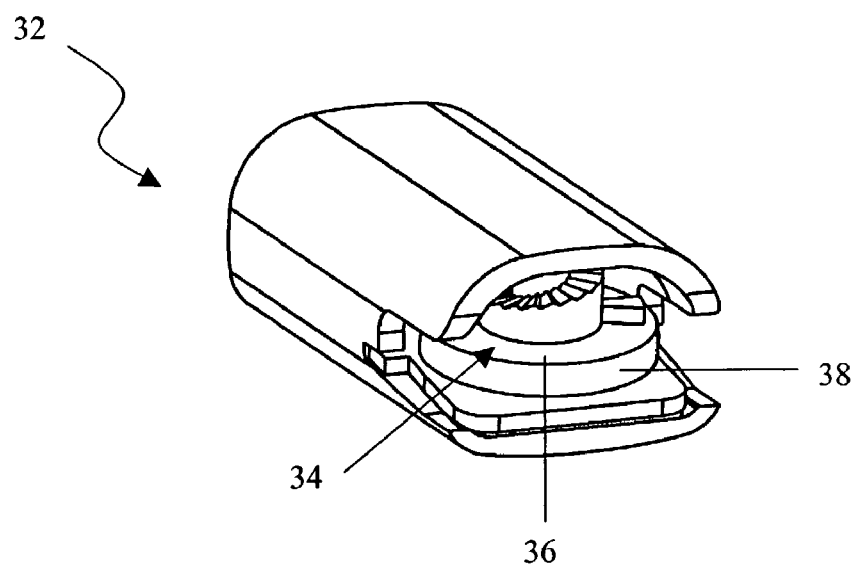
FIG. 1B is a perspective view illustrating the valve mechanism according to one embodiment of the present invention.
Figure 2:
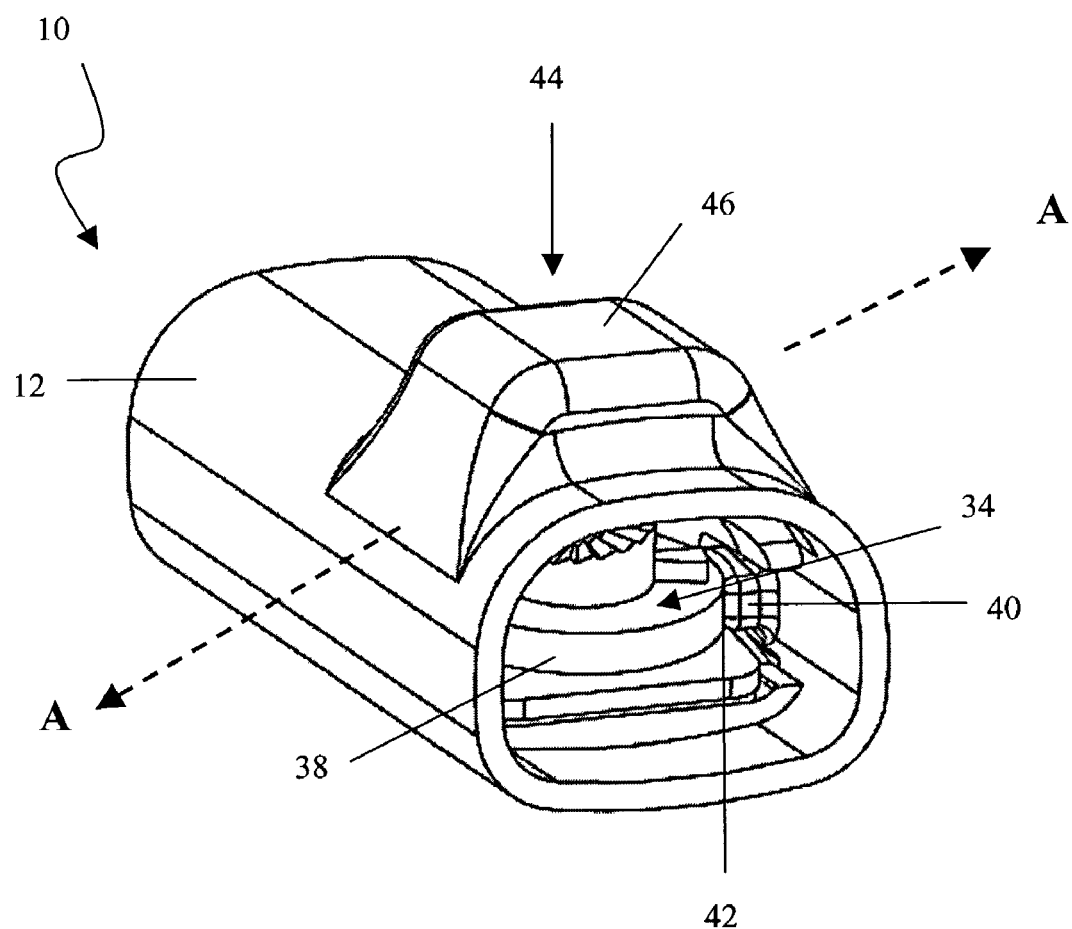
FIG. 2 is a perspective view illustrating the valve mechanism of FIG. 1B with the housing of FIG. 1A according to one embodiment of the present invention.

In a first embodiment, shown in FIGS. 1A-3B, the locking assembly of the present invention can be used in conjunction with a shunt valve system, such as the shunt valve system 10 illustrated in FIG. 2. The locking assembly of the present invention can be used with a variety of shunt valve systems designed to drain excess fluid from one area of the body and direct it to another site in a patient's body. An exemplary shunt valve system for use with the locking assembly of the present invention is a shunt valve system used in a shunt system designed to treat hydrocephalus. In a hydrocephalus shunt system, the shunt valve system 10 is attached to a ventricular catheter (not shown), which is placed within a ventricle of a patient's brain, and a drainage catheter (not shown), which is placed within another area of the patient's body, such as for example, the right atrium of the heart or the peritoneum, where the cerebrospinal fluid (CSF) can be absorbed into the patient's bloodstream. The shunt valve system 10, therefore, controls the flow of excess CSF from the ventricle of the brain to another area of the patient's body.

As shown in FIG. 1A, the shunt valve system 10 used in conjunction with the locking assembly of this first embodiment includes a housing 12 having an outer surface 14 that contacts the target site of implantation and an inner surface 16 that defines a chamber 18. The chamber 18 is adapted to allow fluid to flow through the shunt valve system 10. The chamber 18 of the shunt valve system 10 includes an inlet port (not shown) for receiving fluid into the shunt valve system 10, and an outlet port (not shown) for releasing fluid from the shunt valve system 10. In a typical hydrocephalus shunt system, the inlet port is in fluid communication with the ventricular catheter, while the outlet port is in fluid communication with the drainage catheter.

Referring now to FIG. 1A, the distance between the outer surface 14 and the inner surface 16 defines a thickness of the housing 12. This thickness can vary, but preferably, the thickness of the housing 12 is in the range of about 0.5 to 1.0 mm. The housing 12 of the shunt valve system 10 also includes a first end 20, a second end 22, and a length extending therebetween. The length of the housing 12 can vary, but preferably, the length of the housing 12 is determined according to the dimensions of the target site of implantation. More preferably, the housing 12 has a length in the range of about 2.5 to 5.0 cm.

The housing 12 of the shunt valve system 10 can have virtually any geometry, but preferably, the housing 12 has a generally rectangular shape, as illustrated in FIG. 1A. In this embodiment, the housing 12 includes a top surface 24, a bottom surface 26, and opposed side surfaces 28, 30, as seen in FIG. 1A. The distance between the top surface 24 and bottom surface 26 defines a height $H_1$ of the housing 12, which can vary, but is preferably in the range of about 4.5 to 6.0 mm. Similarly, the distance between the opposed side surfaces 28, 30 defines a width of the housing 12. This width can vary, but preferably, the width of the housing 12 is in the range of about 7.0 to 10.0 mm. Preferably, the geometry and dimensions of the housing 12 of the shunt valve system 10, and in particular, the height, width, and length of the housing 12, are determined according to the proportions of the target site of implantation.

Referring now to FIGS. 1B and 2, the housing 12 of the shunt valve system 10 is designed to surround a fluid regulator, such as for example, the shunt valve mechanism 32 illustrated in FIG. 1B, which is effective to control fluid flow through the shunt valve system 10. The locking assembly of the present invention can be used in conjunction with virtually any shunt valve mechanism 32 that is effective to control fluid flow, but preferably, the shunt valve mechanism 32 includes a differential pressure valve, which regulates the flow of fluid according to a pressure differential created between the inlet and outlet ports of the shunt valve system 10. Thus, a pressure differential valve establishes a pressure threshold, which must be met before fluid begins to flow through the shunt valve system 10. Preferably, the shunt valve mechanism 32 is also adapted to allow a clinician to non-invasively adjust the pressure threshold at which fluid begins to flow through the shunt valve system 10.

An exemplary embodiment of the shunt valve mechanism 32, illustrated in FIGS. 1B-3B, is commonly referred to as a ball-in-cone mechanism, such as for example, the Hakim shunt valve mechanism disclosed by U.S. Pat. No. 4,615,691, the contents of which are hereby incorporated in their entirety by reference. In a typical ball-in-cone shunt valve mechanism 32, the pressure threshold at which fluid begins to flow through the shunt valve system 10 is regulated by a sphere, which is seated in a circular orifice and is effective to block fluid flow through the orifice until the established pressure threshold has been met. The sphere is operatively joined to a first end of a cantilevered spring, while the second end of the spring is operatively joined to a rotor assembly 34, such as the rotor assembly 34 shown in FIGS. 1B-3B. The rotor assembly 34 typically includes a stair-step array, generally in the shape of a spiral staircase, for engaging the second end of the spring. As the rotor assembly 34 is rotated, the second end of the spring moves up or down each stair of the spiral stair array, which results in a corresponding change in the deflection of the cantilevered spring. The change in the angle of deflection of the spring, in turn, alters the force that is exerted by the spring on the sphere. A change in the forced applied by the spring to the sphere results in a corresponding increase or decrease of the established pressure threshold at which fluid begins to flow through the shunt valve system 10.

Preferably, the ball-in-cone shunt valve mechanism 32 used in the present invention is adapted to allow a clinician to adjust the pressure threshold by rotating the rotor assembly 34 in a non-invasive manner. The rotor assembly 34 of the shunt valve mechanism 32 includes at least one magnet carried in a housing 36 having an outer wall 38 (FIGS. 1B-3B), and optionally, an opposed, inner wall (not shown). This magnet allows the clinician to non-invasively adjust the rotor assembly 34 by applying a strong external magnetic field to the shunt valve system 10, and then rapidly switching the field, which causes the rotor assembly 34 to turn. As described above, when the rotor assembly 34 is turned, the second end of the spring is moved up or down the stair-step array, which ultimately results in a change in the pressure threshold of the shunt valve mechanism 32.

In one aspect of the present invention, the locking assembly can effectively prevent the rotor assembly 34 of the shunt valve mechanism 32 from rotating. Such a locking feature can be advantageous to prevent the rotor assembly 34 from inadvertent and undesirable rotation due to environmental magnetic forces. For example, when the shunt valve mechanism 32 is subjected to strong external magnetic forces, such as during MRI procedures, these magnetic forces can cause unanticipated rotation of the rotor assembly 34. The present invention overcomes this problem by providing a locking assembly that is not affected by magnetic forces.

Figure 3A:
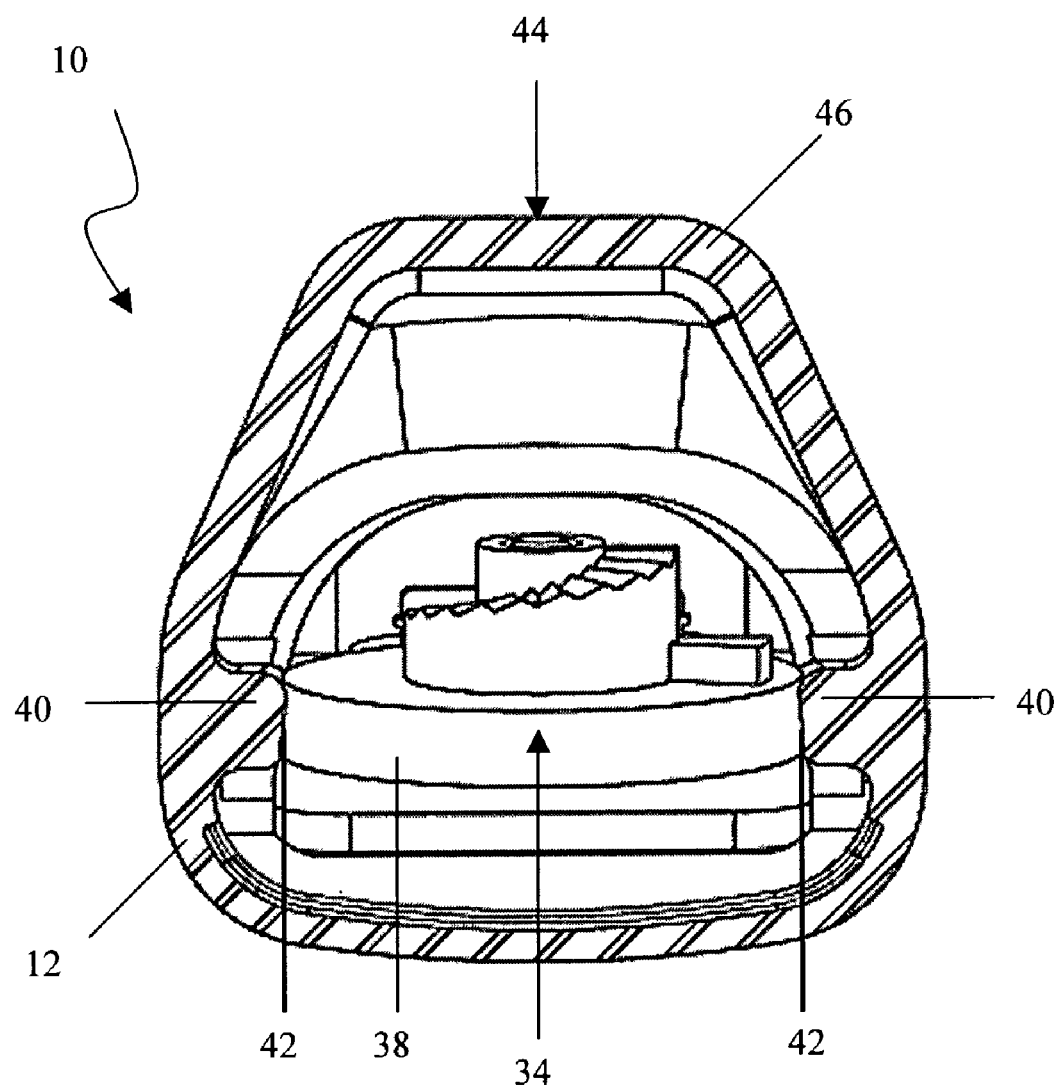
FIG. 3A is a cross-sectional view through lines A-A of the locking assembly of FIG. 2 in an engaged state according to one embodiment of the present invention.
Figure 3B:
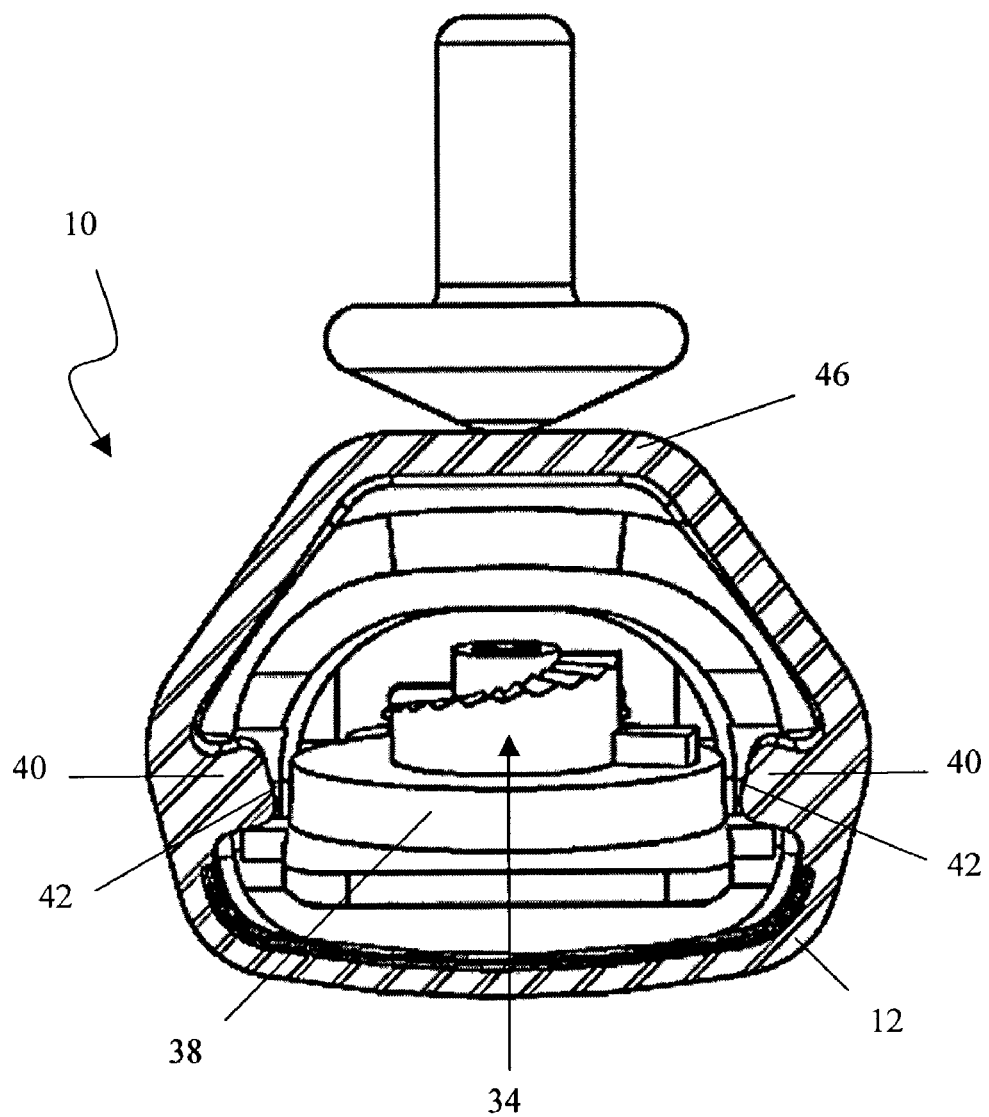
FIG. 3B is a cross-sectional view through lines A-A of the locking assembly of FIG. 2 in a disengaged state according to one embodiment of the present invention.

The locking assembly of the present invention includes at least one gripping arm 40, which can frictionally engage at least a portion of the rotor assembly 34 to prevent the rotor assembly 34 from rotating, even in the presence of strong external magnetic forces. The locking assembly can include virtually any number of gripping arms 40, but preferably, the locking assembly includes opposed, bilateral gripping arms 40, as shown in FIGS. 3A and 3B. To prevent the rotor assembly 34 from rotating, these gripping arms 40 can frictionally engage at least a portion of the rotor assembly 34 and can apply compressive forces to at least a portion of the rotor assembly 34.

Each gripping arm 40 can protrude from the inner surface 16 of the housing 12 of the shunt valve system 10, as shown in FIGS. 1A and 2-3B. The gripping arms 40 of the locking assembly and the housing 12 of the shunt valve system 10 may be integrally formed, or alternatively, the gripping arms 40 and the housing 12 may comprise separate members that have been mated together. A variety of mating techniques known to those having ordinary skill in the art can be used to couple the housing 12 and the gripping arms 40. By way of non-limiting example, the gripping arms 40 can be welded, ultrasonically bonded, adhesively attached or mechanically mated to the housing 12 of the shunt valve system 10.

As shown in FIG. 1A, each gripping arm 40 has at least one rotor contacting surface 42 that is designed to frictionally engage at least a portion of the rotor assembly 34. The dimensions and geometry of each rotor contacting surface 42 can vary. Preferably, each rotor contacting surface 42 is sufficiently sized and configured to mate with a portion of the rotor assembly 34. The contacting surface 42 should be able to maintain the rotor assembly 34 in a static position and counteract any external force urging the rotation of the rotor assembly 34, i.e., provide a braking force which holds the rotor assembly 34 stationary. In one embodiment, the rotor contacting surface 42 can mate with and frictionally engage the outer wall 38 of the rotor assembly 34, as shown in FIG. 3A to stably maintain the rotor assembly 34 in a desired, stationary position. In another embodiment, not shown in the accompanying figures, the rotor contacting surface 42 can mate with and frictionally engage the inner wall (not shown) of the rotor assembly 34, and in yet another embodiment, also not shown in the accompanying figures, the rotor contacting surface 42 can mate with and frictionally engage both the outer wall 38 and the opposed, inner wall (not shown) of the rotor assembly 34.

In an embodiment where the rotor contacting surface 42 frictionally engages the outer wall 38 of the rotor assembly 34, the outer wall 38 may be smooth, as shown in FIGS. 1B-3B, or alternatively, it can include friction-increasing surface features (not shown). The outer wall 38 can include virtually any surface feature that can increase the friction of the outer wall 38. By way of non-limiting example, suitable friction-increasing surface features include grooves, detents, ridges, corrugations, roughened surfaces and combinations thereof. In an embodiment where the rotor contacting surface 42 frictionally engages the inner wall (not shown) of the rotor assembly 34, either alone or in conjunction with the outer wall 38, the inner wall can be smooth, or alternatively, it can include virtually any surface feature that can increase the friction of the inner wall. Suitable friction-increasing surface features include, but are not limited to grooves, detents, ridges, corrugations, roughened surfaces and combinations thereof. In either of these embodiments, the rotor contacting surface 42 can be smooth, or alternatively, it can include friction-increasing surface features (not shown), such as the friction-increasing surface features described above. Preferably, the friction-increasing surface features of the rotor contacting surface 42 are designed to mate with corresponding surface features located on the outer wall 38 of the rotor assembly 34, the inner wall of the rotor assembly, or both walls of the rotor assembly 34.

Actuation of the gripping arms 40 can be achieved by applying an external pressure force to an actuating mechanism 44. The actuating mechanism 44 is configured so that the force applied thereto travels through the housing 12 of the shunt valve system 10 and to the gripping arms 40, deforming the housing 12 and enabling the release of the arms 40 from the rotor assembly 34. Alternatively, the force applied to the actuating mechanism 44 can enable the arms 40 to engage the rotor assembly 34. The actuating mechanism 44 of the locking assembly can have a variety of configurations, but preferably, the actuating mechanism 44 is disposed on the housing 12 of the shunt valve system 10. The actuating mechanism 44 and the housing 12 may be integrally formed, or alternatively, the actuating mechanism 44 and the housing 12 may comprise two separate members that have been mated together. A variety of mating techniques known to those having ordinary skill in the art can be used to couple the housing 12 and the actuating mechanism 44 such that forces exerted on the actuating mechanism 44 can be transferred to the housing 12 and gripping arms 40. By way of non-limiting example, the actuating mechanism 44 can be welded, ultrasonically bonded, adhesively attached or mechanically mated to the housing 12.

As previously described, the actuating mechanism 44 controls movement of the gripping arm 40 by transferring a force from the actuating mechanism 44 through the housing 12 and to the gripping arm 40, which is integral with, or mated to, the housing 12, as described above. In one embodiment, the system is configured such that the gripping arms 40 are biased to the engaged position. The force applied to the actuating mechanism 44 is sufficient to move the housing 12 from the biased, first state to a deformed, second state, in which the gripping arms 40 are disengaged from contact with any portion of the rotor assembly 34. As the force is applied to the actuating mechanism 44, the width of the housing 12 increases, i.e., buckles, which, in turn, causes the gripping arms 40 to bulge outwardly, as shown in FIG. 3B. As the housing 12 is moved into its second, deformed state, the gripping arms 40 no longer frictionally engage any portion of the rotor assembly 34, and a clinician can adjust the pressure threshold of the shunt valve mechanism 32 by rotating the rotor assembly 34. Upon removal of the force applied to the actuating mechanism 44, the housing 12 returns to the first state in which the gripping arms 40 are biased toward the center of the housing 12 to frictionally engage at least a portion of the rotor assembly 34.

In an alternative embodiment, the system is biased to a disengaged state, in which the rotor contacting surface 42 does not frictionally engage any portion of the rotor assembly 34. Upon application of a force to the actuating mechanism 44, the rotor contacting surface 42 of the gripping arms 40 frictionally engages a portion of the rotor assembly 34. By way of example, in this embodiment, application of a force on the actuating mechanism 44 causes the width of the housing 12 to decrease, which, in turn, causes the gripping arms 40 to contract inwardly, i.e., pinch together, and frictionally engage the rotor assembly 34. As the housing is moved into its second, deformed state, the gripping arms 40 frictionally engage a portion of the rotor assembly 34 to prevent any intentional or unintentional adjustment of the shunt valve mechanism 32.

Upon removal of the force applied to the actuating mechanism 44, the housing 12 returns to its biased, first position in which the gripping arms 40 do not frictionally engage any portion of the rotor assembly 34, i.e., the gripping arms 40 buckle away from the center of the housing 12.

In a preferred embodiment, the actuating mechanism 44 is a deformable membrane 46 disposed on the housing 12 of the shunt valve system 10, as illustrated in FIGS. 1A and 2. The deformable membrane 46 can have virtually any size and shape, but preferably, the deformable membrane 46 is generally shaped as a button, as shown in FIGS. 1A and 2-3B. The deformable membrane 46 of the actuating mechanism 44 and the housing 12 of the shunt valve system 10 may be integrally formed, or alternatively, the deformable membrane 46 and the housing 12 may comprise two separate members that have been mated together using any of the various mating techniques known by those having ordinary skill in the art, as described above.

Preferably, the deformable membrane 46 of the actuating mechanism 44 is sized and shaped to provide at least a tactile cue of the location of the shunt valve system 10 after implantation within a patient. To provide a tactile cue, the deformable membrane 46 preferably protrudes above the housing 12 by a height $H_2$, as seen in FIG. 1. In this embodiment, the height $H_2$ of the deformable membrane 46 is preferably in the range of about 1.0 to 3.0 mm. In other embodiments, the deformable membrane 46 can also be configured to provide a visual cue, such as for example a visible bulge that can indicate the location of the shunt valve system 10 within a patient. Additionally, the deformable membrane 46 of the actuating mechanism 44 can be adapted to include an audible cue that can indicate when the gripping arms 40 of the locking assembly are in an engaged state, i.e., when gripping arms 40 frictionally engage a portion of the rotor assembly 34. For example, the deformable membrane 46 can include a preformed spring which can be configured to produce an audible sound, such as a clicking noise, as pressure is applied to the actuating mechanism 44 to deploy the gripping arm 40.

The locking assembly of the present invention and the shunt valve system 10 used in conjunction with the locking assembly of the present invention can be constructed from virtually any biocompatible material. For example, the housing 12 of the shunt valve system 10 can be formed from virtually any biocompatible material, but preferably, the housing 12 is constructed from any suitable, flexible biocompatible material, such as for example, silicone, Dow Corning SILASTIC® BioMedical Grade Liquid Silicone Rubber, polyurethane, nylon, polyethersulfone, and combinations thereof. Additionally, the gripping arms 40 of the locking assembly can be formed from virtually any suitable biocompatible material. Suitable biocompatible materials for constructing the gripping arms 40 include, but are not limited to, flexible materials, such as for example, silicone, Dow Corning SILASTIC® BioMedical Grade Liquid Silicone Rubber, polyurethane, nylon, polyethersulfone, and combinations thereof. In one optional embodiment, the gripping arm 40 can be constructed to form a deformable membrane containing a gel medium therein. In this embodiment, the deformable membrane of the gripping arm 40 can be constructed from virtually any suitable, flexible biocompatible material, such as for example, the flexible materials disclosed above.

The deformable membrane 46 of the actuating mechanism 44 can be constructed from a variety of materials, but preferably, the deformable membrane 46 is constructed from a flexible, biocompatible material. Suitable biocompatible materials include, but are not limited to, a silicone elastomer, polyurethane, nylon, and combinations thereof. In another embodiment, the deformable membrane 46 can be constructed from a shape memory material, or alternatively, the deformable membrane 46 can be constructed to include a shape memory material embedded therein. In an embodiment where the deformable membrane 46 includes a shape memory material, the shape memory material is, preferably, a spring wire embedded within the deformable membrane 46. Suitable shape memory materials for use in the present invention include, but are not limited to, shape memory metal alloys and shape memory polymers. Suitable shape memory metal alloys include, but are not limited to, nickel-titanium alloys such as nitinol (TiNi), copper-base alloys such as CuZnAl and CuAlNi, FeNiAl, and combinations thereof. Suitable shape memory polymers, such as for example, modified polycyclooctene, may include thermoplastic networks, thermoset networks, interpenetrating networks, semi-interpenetrating networks, mixed networks and combinations thereof. The shape memory polymers used in the present invention can be linear or branched thermoplastic elastomers having side chains or other dendritic structural elements.

One of ordinary skill in the art will readily appreciate that the shape memory materials, which can be used in the deformable membrane 46 of the present invention, can change their shape from a first, resting shape to a second, memorized shape in the presence of an external stimulus, or external stimuli. By way of non-limiting example, the shape memory materials of the present invention can change their shape in response to a change in temperature, a change in pH, an ionic change, the presence of light, the presence of an electric field, the presence of a magnetic field, the presence of ultrasound, or any combination of these external stimuli.

In another embodiment not illustrated in the accompanying figures, in which the actuating mechanism 44, and in particular, the deformable membrane 46, includes a shape memory material, the actuating mechanism 44 can control the deployment and release of the gripping arm 40, even in the absence of an external force. In this embodiment, the shape memory material of the deformable membrane 46 can change its shape from a first, resting shape to a second, memorized shape in the presence of an external stimulus, or stimuli, as described above. Thus, in this embodiment, the force applied to the actuating mechanism 44 is provided by the change in the shape memory material in the deformable membrane 46. This force travels through the housing 12 and causes the housing 12 to move between a biased, first state and a deformed, second state.

It will be understood that while the above embodiment has been described and shown as having opposed, bilateral arms, the locking assembly according to this first embodiment can include virtually any number of gripping arms 40, provided that the locking assembly 40 includes at least one gripping arm 40.

Figure 4:
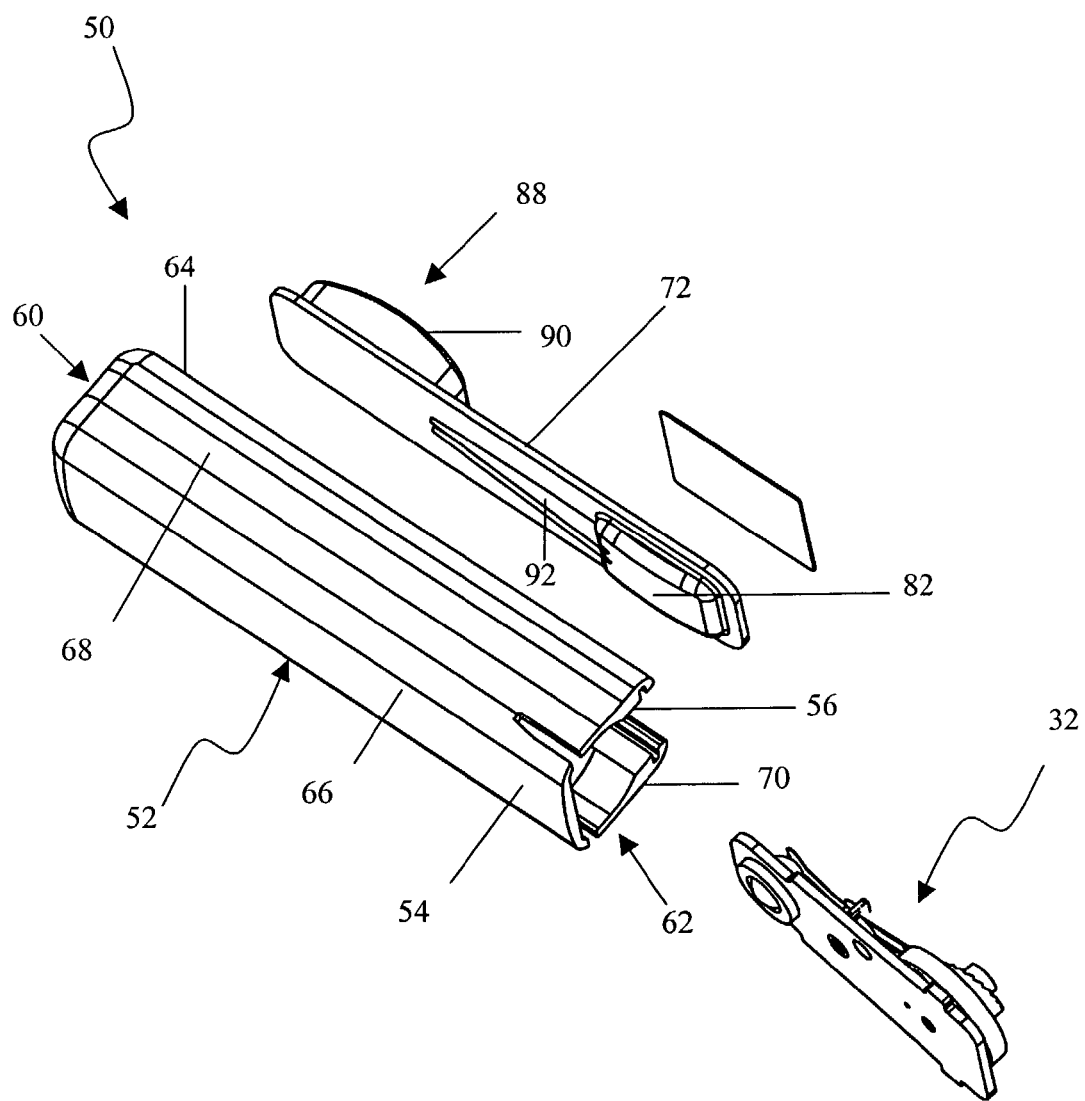
FIG. 4 is an unassembled perspective view illustrating a locking assembly according to another embodiment of the present invention.
Figure 5A:
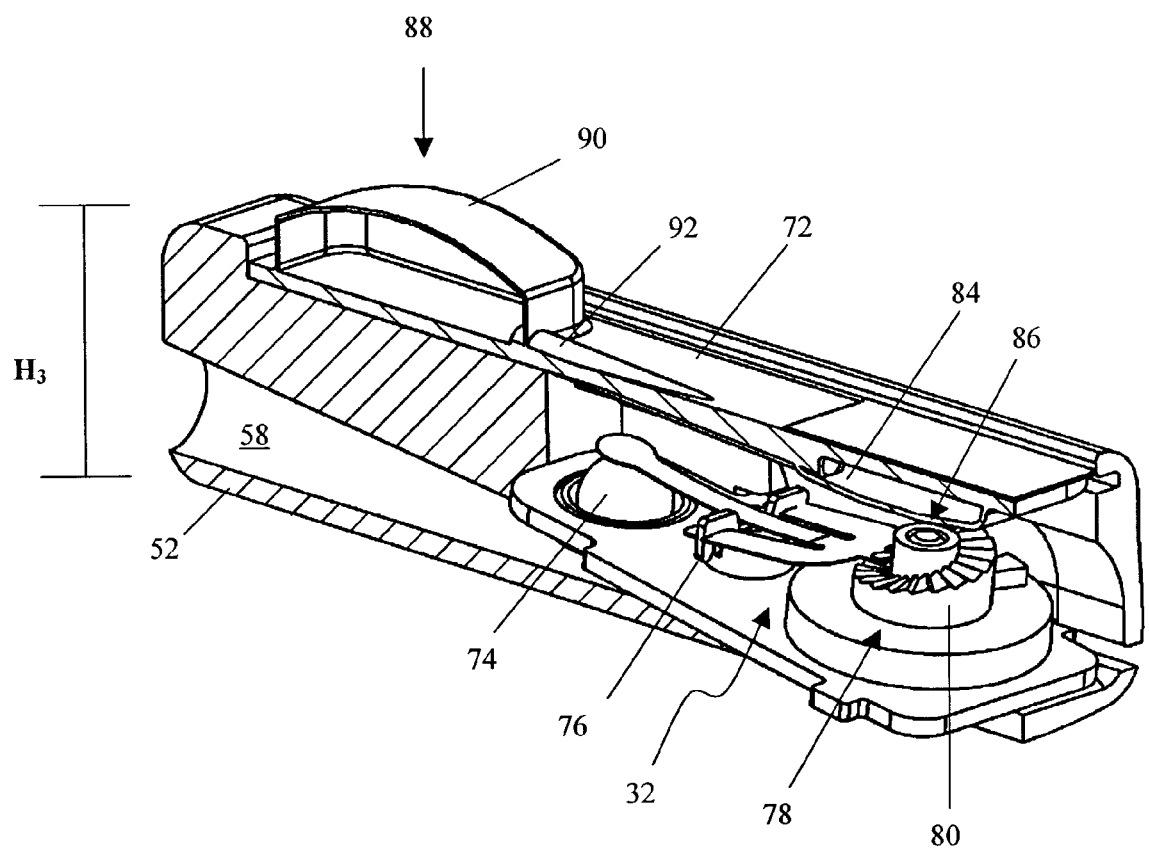
FIG. 5A is a cut-away view of the locking assembly of FIG. 4 in a disengaged state according to another embodiment of the present invention.
Figure 5B:
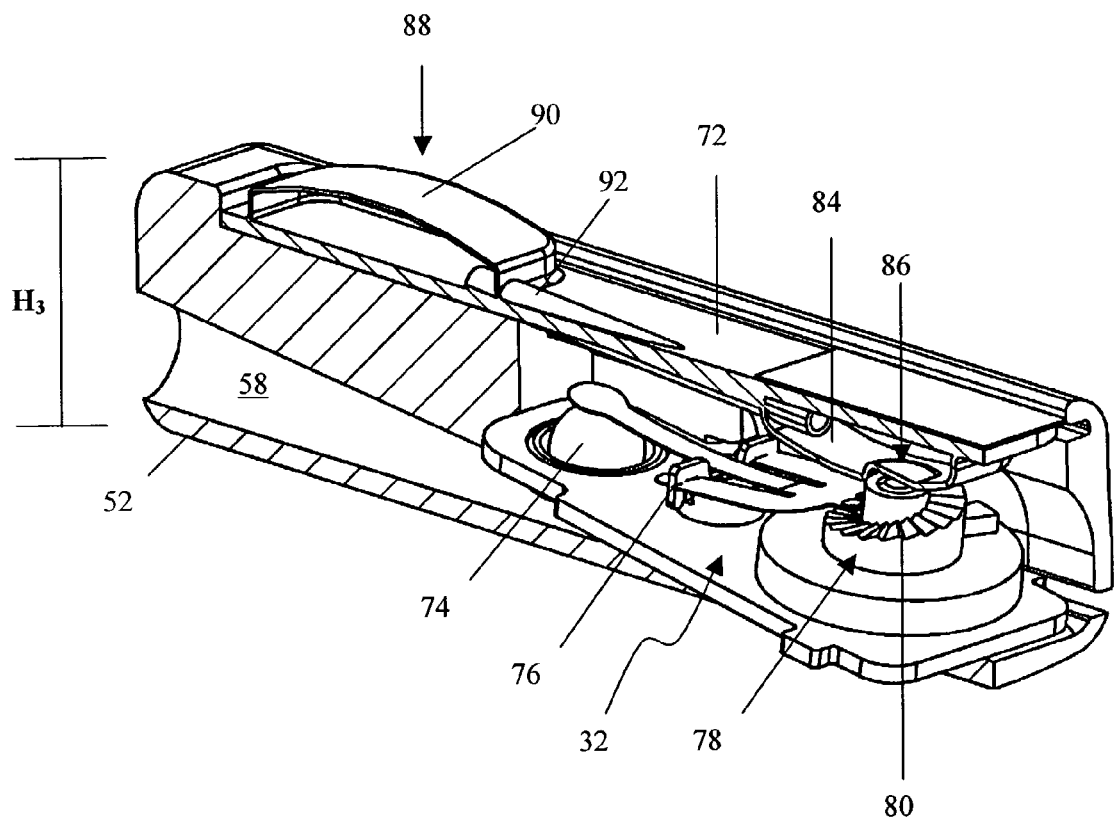
FIG. 5B is a cut-away view of the locking assembly of FIG. 4 in an engaged state according to another embodiment of the present invention.

According to a second embodiment of the locking assembly of the present invention, shown in FIGS. 4-5B, the locking assembly can be used in conjunction with any medical device for regulating the flow of liquid therethrough. For example, the second embodiment of the locking assembly can be used in conjunction with a second embodiment of the shunt valve system described above in connection with the first embodiment of the locking assembly. According to this second embodiment, the shunt valve system 50 includes a housing 52 having an outer surface 54 that contacts the target site of implantation and an inner surface 56 that defines a fluid chamber 58 (FIG. 5A). The fluid chamber 58 is adapted to allow fluid to flow through the shunt valve system 50. The fluid chamber 58 of the shunt valve system 50 includes an inlet port (not shown) for receiving fluid into the shunt valve system 50, and an outlet port (not shown) for releasing fluid from the shunt valve system 50.

Referring now to FIG. 4, the distance between the outer surface 54 and the inner surface 56 defines a thickness of the housing 52. This thickness can vary, but preferably, the thickness of the housing 52 is in the range of about 0.5 to 1.0 mm. The housing 52 of the shunt valve system 50 also includes a first end 60, a second end 62, and a length extending therebetween. The length of the housing 52 can vary, but preferably, the length of the housing 52 is determined according to the dimensions of the target site of implantation. More preferably, the housing 52 has a length in the range of about 2.5 to 5.0 cm.

The housing 52 of the shunt valve system 50 can have virtually any geometry, but preferably, the housing 52 has a generally rectangular shape, as illustrated in FIG. 4. In this embodiment, the housing 52 includes a top surface 64, a bottom surface 66, and opposed side surfaces 68, 70, as shown in FIG. 4. As seen in FIGS. 5A and 5B, the top surface 64 of the housing 52 can be formed as a base 72. This base 72 can be adapted to slidably engage a corresponding groove on the opposed side surfaces 68, 70 of the housing 52. As seen in FIGS. 5A and 5B, the distance between the top surface 64 (or base 72) and bottom surface 66 defines a height $H_3$ of the housing 52, which can vary, but is preferably in the range of about 4.5 to 6.0mm. Similarly, the distance between the opposed side surfaces 68, 70 defines a width of the housing 52. This width can vary, but preferably, the width of the housing 52 is in the range of about 7.0 to 10.0 mm. Preferably, the geometry and dimensions of the housing 52 of the shunt valve system 50, and in particular, the height, width, and length of the housing 52, are determined according to the proportions of the target site of implantation.

As seen in FIGS. 5A and 5B, the housing 52 is designed to surround the shunt valve mechanism 32 described above in connection with the first embodiment of the locking assembly of the present invention. The shunt valve mechanism 32 includes a sphere 74 seated in a circular orifice, a cantilevered spring 76, and a rotor assembly 78. The rotor assembly 78 of the shunt valve mechanism 32 includes a stair-step array 80, generally in the form of a spiral staircase. The stair array 80 of the rotor assembly 78 may be smooth, as shown in FIGS. 5A and 5B, or alternatively, the stair array 80 can include friction-increasing surface features (not shown). The stair array 80 can include virtually any surface feature that can increase the friction of the stair array 80. By way of non-limiting example, suitable friction-increasing surface features include grooves, detents, ridges, corrugations, roughened surfaces and combinations thereof.

In one aspect of the present invention, the locking assembly can effectively prevent the rotor assembly 78 of the shunt valve mechanism 32 from rotating. As discussed above in connection with the first embodiment of the shunt valve system 10, this feature of the locking assembly can be advantageous to prevent the rotor assembly 78 from inadvertent and undesirable rotation due to environmental magnetic forces.

Referring now to FIGS. 4-5B, the locking assembly of the present invention includes at least one gripping arm 82, which can protrude from the inner surface 56 of the housing 52 of the shunt valve system 50. The gripping arm 82 can frictionally engage at least a portion of the stair array 80 of the rotor assembly 78 and can apply a compressive force on a portion of the stair array 80 to stably maintain the rotor assembly 78 in a desired, stationary position, even in the presence of external magnetic forces. The gripping arm 82 can have a variety of configurations, but preferably, the locking assembly includes a single gripping arm 82 that can be formed as at least one inflatable bladder 84. Preferably, the inflatable bladder 84 is disposed on the base 72 of the housing 52 and formed as a button that can deform upon contact with the stair array 80 of the rotor assembly 78, as shown in FIG. 5B. In one embodiment of the present invention, the base 72 of the housing 52 and the gripping arm 82 of the locking assembly may be integrally formed, or alternatively, the base 72 and the gripping arm 82 may comprise two separate members that have been mated together by any of the various mating techniques known to those having ordinary skill in the art.

The gripping arm 82 has at least one rotor contacting surface 86, which can frictionally engage and apply a compressive force to at least a portion of the stair array 80 of the rotor assembly 78, as described above. The dimensions and geometry of each rotor contacting surface 86 can vary. Preferably, each rotor contacting surface 86 is sufficiently sized and configured to engage a portion of the stair array 80 of the rotor assembly 78, as shown in FIG. 5B. The contacting surface 86 should be able to maintain the rotor assembly 78 in a static position and counteract any external force urging the rotation of the rotor assembly 78. The rotor contacting surface 86 can be smooth, or in an alternative embodiment, it can include friction-increasing surface features (not shown). Suitable friction-increasing surface features, include, but are not limited to, grooves, detents, ridges, corrugations, roughened surfaces and combinations thereof.

Actuation of the gripping arm 82 can be achieved by applying an external pressure force to an actuating mechanism 88. The actuating mechanism 88 can have a variety of configurations, but preferably, the actuating mechanism 88 can be formed as a deformable membrane disposed on a base 72, which can be slid into a corresponding groove in the housing 52 of the shunt valve system 50, as seen in FIG. 4. The actuating mechanism 88 can be connected to the gripping arm 82 by a channel 92 to form a closed system, such that the actuating mechanism 88 and the gripping arm 82 are in fluid communication with each other, and application of an amount of force applied to the actuating mechanism 88 transfers an equal amount of force to the gripping arm 82. In the present embodiment illustrated in FIGS. 5A and 5B, the actuating mechanism 88 and the gripping arm 82 can be filled with a gaseous medium such as air, or alternatively, the actuating mechanism 88 and the gripping arm 82 can be filled with a liquid medium that is effective to transfer the applied force from the actuating mechanism 88 to the gripping arm 82. In yet another embodiment, the actuating mechanism 88 and the gripping arm 82 can be filled with a gel medium that can transfer the applied force from the actuating mechanism 88 to the gripping arm 82.

The force transferred from the actuating mechanism 88 to the gripping arm 82 is sufficient to move the gripping arm 82 into and out of a position in which the pressure threshold of the shunt valve mechanism 32 is locked. In one embodiment, the gripping arm 82 is biased to a disengaged condition, shown in FIG. 5A, in which the rotor contacting surface 86 does not frictionally engage any portion of the stair array 80 of the rotor assembly 78. Upon application of a force by the actuating mechanism 88, the gripping arm 82 is moved to an engaged state, shown in FIG. 5B, in which the rotor contacting surface 86 frictionally engages a portion of the stair array 80 of the rotor assembly 78. In this embodiment, application of a force to the actuating mechanism 88 causes the rotor contacting surface 86 of the gripping arm 82 to bulge or expand outwardly from the base 72 of the housing 52. This deformation of the gripping arm 82 is sufficient to cause the rotor contacting surface 86 to frictionally engage the stair array 80 of the rotor assembly, as shown in FIG. 5B. In one embodiment, upon removal of the force applied to the actuating mechanism 88, the gripping arm 82 returns to the first state in which the gripping arm 82 no longer frictionally engages any portion of the rotor assembly 78, as shown in FIG. 5A. In another embodiment, the channel 92 can include a bleeder valve (not shown) that can initially prevent the flow of the fluid, gaseous or gel medium from the gripping arm 82 to the actuating mechanism 88, but can, over time, allow the fluid, gaseous or gel medium to seep back into the actuating mechanism 88.

In a preferred embodiment, the actuating mechanism 88 is a deformable membrane 90 disposed on the base 72 of the shunt valve system 50, as illustrated in FIGS. 4-5B. The deformable membrane 90 can have virtually any size and shape, which are, preferably, designed according to the dimensions of the target site of implantation. In a preferred embodiment, the deformable membrane 90 is generally shaped as a button and is bilaterally opposed to the gripping arm 82, as shown in FIGS. 4 and 5A. The deformable membrane 90 of the actuating mechanism 88 and the base 72 of the shunt valve system 50 may be integrally formed, or alternatively, the deformable membrane 90 and the base 72 may comprise two separate members that have been mated together using any of the various mating techniques known by those having ordinary skill in the art, as described above.

Preferably, the deformable membrane 90 of the actuating mechanism 88 is sized and shaped to provide at least a tactile cue of the location of the shunt valve system 50 implanted within a patient. To provide a tactile cue, the deformable membrane 46 preferably protrudes above the top surface 64 or base 72 of the housing 52, as seen in FIGS. 5A and 5B. In this embodiment, the height of the deformable membrane 90 is preferably in the range of about 1.0 to 3.0 mm. In other embodiments, the deformable membrane 90 can also be configured to provide a visual cue, such as for example a visible bulge that can indicate the location of the shunt valve system 50 within a patient. Additionally, the deformable membrane 90 of the actuating mechanism 88 can be adapted to include an audible cue that can indicate when the gripping arm 82 of the locking assembly is in an engaged state, such that the gripping arm 82 frictionally engages at least a portion of the stair array 80 of the rotor assembly 78. For example, the deformable membrane 90 can include a preformed spring which can be configured to produce an audible sound, such as a clicking noise, as pressure is applied to the actuating mechanism 88 to deploy the gripping arm 82.

The locking assembly of this second embodiment of the present invention can be constructed from virtually any biocompatible material. Suitable biocompatible materials have been described above in connection with the first embodiment of the locking assembly of the present invention.

The deformable membrane 90, in particular, can be constructed from a shape memory material, or alternatively, the deformable membrane 90 can include a shape memory material embedded therein. In an embodiment where the deformable membrane 90 includes a shape memory material, the shape memory material is, preferably, a spring wire embedded within the deformable membrane 90. Suitable shape memory materials for use in the present invention include those discussed above in connection with the first embodiment of the shunt valve system 10. The shape memory materials, which can be used in the deformable membrane 90 of the present invention, are effective to change their shape from a first, resting shape to a second, memorized shape in the presence of an external stimulus, or external stimuli. By way of non-limiting example, the shape memory materials of the present invention can change their shape in response to a change in temperature, a change in pH, an ionic change, the presence of light, the presence of an electric field, the presence of a magnetic field, the presence of ultrasound, or any combination of these external stimuli.

In use, upon the application of an external mechanical force to the actuating mechanism 88, such as the application of force by the clinician on the deformable membrane 90, the fluid, gaseous or gel medium within actuating mechanism 88 is transferred to the inflatable bladder 84 of the gripping arm 82, whereupon the gripping arm 82 bellows out, i.e., becomes enlarged with the additional fluid medium transferred thereto. The expanded gripping arm 82 exerts the additional force upon the stair array 80 of the rotor assembly 78 of the shunt valve mechanism 32 of the shunt valve system 50, as shown in FIG. 5B. The expanded gripping arm 82 thus contacts the stair array 80 of the rotor assembly 78 and applies a compressive force to a portion of the stair array 80 to prevent the rotor assembly 78 from rotating. In one embodiment, the gripping arm 82 and the deformable membrane 90 are resilient, and upon release of the external mechanical force, the fluid media within the gripping arm 82 and the deformable membrane 90 will reach equilibrium and the gripping arm 82 will no longer be expanded. Optionally, the channel 72 can include a bleeder valve (not shown) that can initially prevent the flow of the gaseous, fluid or gel medium from the gripping arm 82 to the actuating mechanism 88, but can, over time, allow the fluid, gaseous or gel medium to seep into the actuating mechanism 88. As the gripping arm 82 deflates and resumes its resting state, the rotor assembly 78 will no longer be constrained by the gripping arm 82 pressing against it. Accordingly, as shown in FIG. 5B, the rotor assembly 78 is free to rotate without encumbrances.

It is contemplated that the gripping arm 82, which is intended to contact the stair array 80 of the rotor assembly 78 upon expansion, can also include friction-increasing surface features upon its outer surface. Suitable friction-increasing surface features include, but are not limited to, grooves, detents, ridges, corrugations, roughened surfaces and combinations thereof. These friction-increasing surface features can cooperatively mate with the stair array 80 of the rotor assembly 78 to provide a further means of preventing the rotation of the rotor assembly 78.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A shunt valve system, comprising:
   a housing having therein a chamber including an inlet port for receiving fluid, an outlet port for fluid release, and a valve mechanism including a rotor assembly for regulating fluid flow therethrough, when a fluid pressure differential between the inlet port and the outlet port exceeds a selected valve opening pressure; and
   a selectively engageable locking assembly formed integrally with a wall of the housing and effective to prevent rotation of the rotor assembly, the locking assembly having at least one protrusion extending from a wall of the housing, the protrusion having at least one contacting surface that is configured to selectively frictionally engage the rotor assembly to selectively maintain the rotor assembly in a desired position.

2. The system of claim 1, wherein the rotor assembly further includes an outer wall, the at least one contacting surface of the at least one protrusion being adapted to frictionally engage the outer wall of the rotor assembly.

3. The system of claim 1, wherein the rotor assembly further includes an inner wall, the at least one contacting surface of the at least one protrusion being adapted to frictionally engage the inner wall of the rotor assembly.

4. The system of claim 1, wherein the locking assembly further includes an actuating mechanism for releasing and deploying the at least one protrusion.

5. The system of claim 4, wherein the actuating mechanism comprises a deformable membrane disposed on the housing that is configured to transfer a force applied to the deformable membrane though the housing and to the at least one protrusion sufficient to move the at least one protrusion between a first state in which the at least one protrusion frictionally engages the rotor assembly and a second state in which the at least one protrusion is disengaged from the rotor assembly.

6. The system of claim 5, wherein the deformable membrane is formed from an elastomeric material selected from the group consisting of a silicone elastomer, polyurethane, nylon, and combinations thereof.

7. The system of claim 5, wherein the deformable membrane of the actuating mechanism includes a shape memory material.

8. The system of claim 1, wherein the locking mechanism contains opposed, bilateral protrusions.

9. The system of claim 2, wherein the outer wall of the rotor assembly contains friction-increasing surface features selected from the group consisting of grooves, detents, ridges, corrugations, roughened surfaces and combinations thereof.

10. The system of claim 3, wherein the inner wall of the rotor assembly contains friction-increasing surface features selected from the group consisting of grooves, detents, ridges, corrugations, roughened surfaces and combinations thereof.

11. The system of claim 1, wherein the at least one protrusion has an outer surface containing friction-increasing surface features selected from the group consisting of grooves, detents, ridges, corrugations, roughened surfaces and combinations thereof.

12. A shunt valve system, comprising:
   a housing having therein a chamber including an inlet port for receiving fluid, an outlet port for fluid release, and a valve mechanism including a rotor assembly for regulating fluid flow therethrough, when a fluid pressure differential between the inlet port and the outlet port exceeds a selected valve opening pressure; and
   a selectively engageable locking assembly for preventing rotation of the rotor assembly, the locking assembly having at least one protrusion having at least one contacting surface that is adapted to frictionally engage the rotor assembly to selectively maintain the rotor assembly in a desired position, the protrusion formed as an inflatable bladder.

13. A shunt valve system, comprising:
   a housing having therein a chamber including an inlet port for receiving fluid, an outlet port for fluid release, and a valve mechanism including a rotor assembly for regulating fluid flow therethrough, when a fluid pressure differential between the inlet port and the outlet port exceeds a selected valve opening pressure; and
   a selectively engageable locking assembly for preventing rotation of the rotor assembly, the locking assembly having at least one protrusion having at least one contacting surface that is adapted to frictionally engage the rotor assembly to selectively maintain the rotor assembly in a desired position, wherein the locking assembly further includes an actuating mechanism for releasing and deploying the at least one protrusion, the actuating mechanism comprising a deformable membrane disposed on the housing that is configured to transfer a force applied to the deformable membrane through the housing and to the at least one protrusion sufficient to move the at least one protrusion between a first state in which the at least one protrusion frictionally engages the rotor assembly and a second state in which the at least one protrusion is disengaged from the rotor assembly, the deformable membrane of the actuating mechanism including a shape memory material, wherein the shape memory material is a spring wire embedded within the deformable membrane.

* * * * *